US011432731B2

(12) United States Patent
Chun et al.

(10) Patent No.: US 11,432,731 B2
(45) Date of Patent: Sep. 6, 2022

(54) ULTRA-LOW PROFILE WIRELESS FLOW SENSORS TO MONITOR HEMODYNAMIC ALTERATIONS IN THE VASCULAR SYSTEM

(71) Applicants: University of Pittsburgh-Of the Commonwealth System of Higher Education, Pittsburgh, PA (US); Virginia Commonwealth University, Richmond, VA (US)

(72) Inventors: Young Jae Chun, Pittsburgh, PA (US); Brian T. Jankowitz, Pittsburgh, PA (US); Sung Kwon Cho, Pittsburgh, PA (US); Yanfei Chen, Pittsburgh, PA (US); Woon-Hong Yeo, Glen Allen, VA (US); Yongkuk Lee, Richmond, VA (US); Connor Howe, Richmond, VA (US)

(73) Assignees: UNIVERSITY OF PITTSBURGH—OF THE COMMONWEALTH SYSTEM OF HIGHER EDUCATION, Pittsburgh, PA (US); VIRGINIA COMMONWEALTH UNIVERSITY, Richmond, VA (US)

( * ) Notice: Subject to any disclaimer, the term of this patent is extended or adjusted under 35 U.S.C. 154(b) by 503 days.

(21) Appl. No.: 16/303,190

(22) PCT Filed: May 26, 2017

(86) PCT No.: PCT/US2017/034628
§ 371 (c)(1),
(2) Date: Nov. 20, 2018

(87) PCT Pub. No.: WO2017/205718
PCT Pub. Date: Nov. 30, 2017

(65) Prior Publication Data
US 2019/0167120 A1 Jun. 6, 2019

Related U.S. Application Data

(60) Provisional application No. 62/342,507, filed on May 27, 2016.

(51) Int. Cl.
*A61B 5/026* (2006.01)
*A61B 5/021* (2006.01)
*A61B 5/00* (2006.01)

(52) U.S. Cl.
CPC .......... *A61B 5/026* (2013.01); *A61B 5/0002* (2013.01); *A61B 5/021* (2013.01); *A61B 5/6852* (2013.01);
(Continued)

(58) Field of Classification Search
CPC ....... A61B 5/021; A61B 5/026; A61B 5/6852; A61B 5/6862; A61B 2562/12; A61F 2250/0096
See application file for complete search history.

(56) References Cited

U.S. PATENT DOCUMENTS 7,279,664 B2 * 10/2007 Weber .................. A61F 2/86
219/635
7,677,107 B2 3/2010 Nunez et al.
(Continued)

*Primary Examiner* — Devin B Henson
(74) *Attorney, Agent, or Firm* — Carol A. Marmo; Eckert Seamans Cherin & Mellott, LLC

(57) ABSTRACT

The invention relates to endovascular medical implant devices, systems and methods that including a sensing device and a flow diverter device, which are effective to monitor intra-/post-operative hemodynamic properties in the location of a cerebral aneurysm and, hemodynamic alterations following placement of the system for treating ischemic diseases in carotid, coronary and peripheral arteries.
(Continued)

The sensing device includes wireless, non-thrombogenic, highly stretchable, ultra-low profile flow sensors.

13 Claims, 5 Drawing Sheets

(52) U.S. Cl.
CPC ........ *A61B 5/6862* (2013.01); *A61B 2562/12* (2013.01)

(56) References Cited

U.S. PATENT DOCUMENTS

| | | |
|---|---|---|
| 10,869,748 B2 * | 12/2020 | Rosenberg ................. A61F 2/07 |
| 2006/0106451 A1 | 5/2006 | Busiashivili |
| 2013/0041244 A1 | 2/2013 | WOlAS et al. |
| 2013/0053711 A1 * | 2/2013 | Kotlanka ................. G01F 1/28 |
| | | 600/505 |
| 2013/0178750 A1 | 7/2013 | Sheehan et al. |
| 2013/0226034 A1 | 8/2013 | Stein et al. |
| 2014/0081154 A1 | 3/2014 | Toth |
| 2014/0350348 A1 | 11/2014 | Tee et al. |
| 2015/0320357 A1 * | 11/2015 | Kuraguntla ............... A61F 2/07 |
| | | 600/505 |
| 2016/0022222 A1 | 1/2016 | Folk et al. |
| 2016/0022447 A1 | 1/2016 | Kim et al. |
| 2016/0302729 A1 * | 10/2016 | Starr ................. A61B 5/02158 |

* cited by examiner

ULTRA-LOW PROFILE WIRELESS FLOW SENSORS TO MONITOR HEMODYNAMIC ALTERATIONS IN THE VASCULAR SYSTEM

CROSS REFERENCE TO RELATED APPLICATIONS

This application is a U.S. National Stage Application under 35 U.S.C. *§ 371 of PCT International Application No. PCT/US2017/034628, entitled "NOVEL ULTRA-LOW PROFILE WIRELESS FLOW SENSORS TO MONITOR HEMODYNAMIC ALTERATIONS IN THE VASCULAR SYSTEM," filed on May 26, 2017, which claims priority under 35 U.S.C. § 119(e) from U.S. provisional patent application No. 62/342,507, entitled "NOVEL ULTRA-LOW PROFILE WIRELESS FLOW SENSORS TO MONITOR HEMODYNAMIC ALTERATIONS IN THE VASCULAR SYSTEM," filed on May 27, 2016, the contents of which are incorporated herein by reference.

1. FIELD OF THE INVENTION

The invention relates generally to devices, systems and methods to monitor hemodynamic alterations in the vascular system and, more particularly, to ultra-low profile wireless microflow sensors to measure blood flow in the vascular system. The invention is particularly useful to monitor intra-/post-operative hemodynamic properties in the location of a cerebral aneurysm and, hemodynamic alterations following device placement for treating ischemic diseases in carotid, coronary and peripheral arteries. The invention, more particularly, includes ultra-low profile, highly stretchable, non-thrombogenic, microflow sensors.

2. Background

The introduction of minimally invasive surgical techniques and the development of various endovascular devices have substantially improved human health care over several decades. Further improvements may be realized by increasing the functionality of these devices and extending the types of procedures where such devices may be employed.

Cerebral aneurysms occur when a weakened area of a blood vessel allows blood to flow into a sac or ballooned section outside of its normal flow path. The reported prevalence of unruptured cerebral aneurysms is about 3.6% to 6% of the population. While it is common for patients with unruptured aneurysms to be asymptomatic, the aneurysm represents the potential for a rupture or leak to develop which results in hemorrhagic stroke, permanent nerve damage, or death. The risk of rupture is about 1% per year, resulting in a lifetime risk of about 20-50%. Cerebral aneurysm rupture carries an extremely high rate of morbidity and a mortality rate of up to about 50%. Effective monitoring and early treatment is therefore critical to preventing further complications from arising.

Standard treatment for cerebral aneurysms currently includes surgical clipping or endovascular embolization. Endovascular coiling has largely replaced the highly invasive clipping due to its lower initial risk, dependency and mortality. While coiling, e.g., with platinum coils, is much less invasive and has lower risk, the cure rates are not as successful due to persistent blood flow causing recanalization in the aneurysmal sac and recurrences in up to about 26.8% of cases. Theoretically, an aneurysm is not cured until intra-aneurysmal flow is reduced enough to allow endothelialization or healing of the aneurysm neck, effectively sealing the pouch, and eliminating any blood flow into the aneurysm.

The shortcomings of these standard treatments elucidate the need for a novel approach to treatment of a cerebral aneurysm with a focus on the ease and availability of maintaining minimally invasive, persistent and routine monitoring of incoming blood flow to the treated aneurysm to reduce the risk of post-intervention dependence and death.

A more recent and compelling treatment technique is the use of a flow diverter which is placed inside the vessel adjacent to the aneurysm. A flow diverter effectively reduces blood flow into the aneurysm and clinical outcome has seen a complete occlusion rate of 76%. Complete occlusion of the aneurysm after treatment significantly reduces the risk of a rupture compared to partial occlusion. Especially in cases of a ruptured aneurysm, complete occlusion has shown risk of re-rupture to be 1.1%, and 17.6% for a partial occlusion (less than 70% occlusion). This suggests a clear benefit for the availability of easy, low impact, long term monitoring of the treatment.

It is known in the art that it is necessary to measure intra-/post-operative hemodynamic quiescence. The recurrence rate is high enough to require long term follow-up imaging, often necessitating repeated invasive catheter-based angiograms. The expense and risk of continued follow-up imaging, combined with the general anxiety about potential aneurysm recurrence is often used by traditional surgeons to favor open surgery. Similar phenomenon also has occurred after the treatment of cerebral aneurysm using recently developed flow diverter devices. Flow monitoring after the device deployment is critical to evaluate the progress of the curing process.

Since, there are barriers to coil therapy success and disadvantages associated with current implantable sensors, a non-invasive method to monitor and definitively prove aneurysm healing would be of significant importance in various diseases including, but not limited to, the three ischemic vascular diseases described as follows.

Carotid Artery Ischemic Disease

Stroke and atherosclerotic cerebrovascular disease represents a significant disease burden in the United States, showing the third most common cause of mortality. The American Stroke Association estimated $73.7 billion dollars spent in 2010 for the direct and indirect costs generated by stroke. Epidemiological studies have estimated the prevalence of stroke approximately 795,000 people every year and approximately 30% of them have been attributed to atherosclerotic carotid bifurcation disease. The deposits of thrombosis, cholesterol or atherosclerosis in the narrowed or blocked carotid arteries sometimes break off from the plaque and enter the cerebral circulation (i.e., embolization). The thrombotic emboli and cholesterol fragments can get caught in a smaller cerebral blood vessel generating ischemic stroke.

Two common approaches currently used to treat carotid artery stenosis include open surgery (i.e., endarterectomy) and endovascular procedure (i.e., balloon angioplasty and placement of stents with separate embolic protection filter devices). Endarterectomy remains the gold standard of treating atherosclerotic carotid artery stenosis due to its safety, effectiveness and durability (i.e., reduced risk of stroke). However, because the endovascular procedure is less invasive and more cost effective than open surgery, it has become popular in the last decade especially for high-risk patients with severe carotid stenosis. Recent studies on comparing carotid endarterectomy and endovascular treatment showed that stenting with distal embolic protection is a reasonable revascularization strategy in carotid artery disease. A recent Carotid Revascularization Endarterectomy versus Stenting Trial (CREST) found that the rate of stroke or death with stenting was higher than that with endarterectomy. Stenting carries a significantly higher risk of periprocedural ipsilateral stroke. Although carotid artery stenting may cause more strokes, several studies have indicated that the two procedures are equivalent, because the overall outcomes remain equivalent at a longer period, e.g., 2 to 4 years.

Coronary Artery Disease (CAD)

Coronary artery disease (CAD) is the most common type of heart disease and the leading cause of death worldwide. The disease is caused by plaques building up in the coronary arteries, which narrows the artery and prevents adequate blood supply to the myocardium. CAD was responsible for approximately 20% of all deaths in 2005 in the United States, according to the American Heart Association. Among the interventions to restore blood flow, angioplasty (removal or compression of the plaque by use of catheter, balloon or stent) and bypass grafting (detouring around the blockage) are mostly well established methods for treating CAD. In 2006, approximately 652,000 patients in the US were treated using coronary intervention surgery with stent implantation with an approximately total cost of about $31 billion.

Clinically applied bare metal stents (BMS) are usually made of non-degradable metallic materials, such as 316 stainless steel, tantalum, cobalt-chromium alloy and titanium alloy. The initial clinical results of BMS are generally quite attractive. However, re-narrowing of the treated artery is commonly observed in approximately 20% to 30% of patients. This re-narrowing of the treated artery is due to restenosis, which results from excessive smooth muscle proliferation. Acute occlusion by thrombosis presents another limitation in the application of BMS. Drug eluting stents (DES) have been developed by incorporating antiproliferative agents and markedly improved clinical outcomes by reducing the rate of restenosis. The sirolimus eluting Cypher stent using stainless steel and a biostable polymer coating (Cordis/J&J) received FDA approval in 2003. Afterwards, the paclitaxel eluting Taxus stent (Boston Scientific), the zotarolimus eluting Endeavor stent (Medtronic), and XIENCE V™ everolimus drug eluting stent (Abbott) were approved for clinical trials by the FDA.

Peripheral Arterial Disease (PAD)

Lower extremity peripheral arterial disease (PAD) represents a significant disease burden in the United States. Epidemiological studies have estimated the prevalence of PAD at between approximately 3% to 10% with an increase to approximately 10% to 15% in persons over 70 years old. Industry wide estimates suggest that for femoral and popliteal disease alone, there will be an increase to about 1.7 million procedures by 2020. Current treatment trends for PAD include an expanding role for endovascular procedures to revascularize ischemic limbs as compared to open bypass. Recently a randomized trial in patients with chronic limb ischemia revealed no difference in amputation free survival at one year between endovascular versus open bypass surgery. However, open surgical repair using vein graft remains the gold standard of treating complex lesions in the extremities due to better long term patency (i.e. reduced thrombogenicity). Therefore, a critical need exists for developing endovascular technology to treat PAD that is non-thrombogenic or at least comparable to vein grafts.

A neurovascular catheter is typically used to deliver a flow diverter to the site of a cerebral aneurysm. While this technique is significantly less invasive and safer compared to conventional treatment methods, it presents a challenge in that it can cause the flow diverter's metal film to undergo extreme radial deformation of 400-500% and extreme bending (180°) as it navigates the highly tortuous vessels. For this reason it is imperative that the device be flexible and stretchable to accommodate utilization in the cerebral blood vessels.

There are known wireless sensors which are commercially available and suitable for long-term, continuous monitoring of blood pressure changes, e.g., ISSYS, CardioMEMS Endo Sensor, and DSI-PA. While these implantable sensors have suitable size for both cardiovascular and aortic applications, they are significantly bulky and not sufficiently flexible for use in cerebral endovascular procedures, which typically require a 1.7 Fr microdelivery catheter (i.e., OD=0.56 mm). In addition, these sensors only monitor pressure changes (not flow velocity reductions), which is not suitable for monitoring intra-aneurysmal hemodynamic quiescence, because the primary concept of endovascular coiling as a treatment for cerebral aneurysms is based on the localized thrombus formation within the sac by the attenuated entering flow (i.e., not pressure). Recent experimental studies have revealed that coiling therapy did not attenuate mean intra-aneurysmal pressures, because the cyclic systolic pressure was distributed evenly throughout the aneurysmal wall, while the intra-aneurysmal flow velocity was reduced due to the flow disturbance by coil deployment. In addition, currently available implantable wireless sensors are designed for cardiac or abdominal regions where the distance between the sensor and receiver is short. However, cerebral aneurysms occur within the subarachnoid spaces of the brain, which is surrounded by thick tissue and skull (e.g., 10 to 15 cm below the skin). Therefore, there exists challenging design issues for the intracranial environment, such as, the physical dimension of sensors, mechanical property, measurement range, sensitivity and packaging.

Due to the re-narrowing of an artery following stent implantation, repeated follow-up angiography or Doppler measurement are required for a patient, which can be invasive and expensive. Thus, there is a need in the art to develop endovascular devices and systems that provide capability for non-invasive monitoring of hemodynamic alterations in a vascular system on a continuous basis. A low-profile wireless flow sensor-equipped stent can monitor blood flow continuously by providing the information on re-narrowing of a treated blood vessel, e.g., the velocity of blood flow increases with re-narrowing.

SUMMARY OF THE INVENTION

In one aspect, the invention provides an endovascular medical implant system positioned in a vascular system of a patient, including a flow diverting device, comprising a thin film nitinol; and a wireless, non-thrombogenic, highly stretchable, ultra-low profile, microflow capacitive sensor component connected to at least a portion of the flow diverting device, which includes a first metallic layer; a dielectric elastomer layer deposited on the first metallic layer; and a second metallic layer deposited on the dielectric elastomer layer.

Each of the first and second metallic layers can be selected from the group consisting of gold, magnesium, nitinol and blends thereof.

The flow diverting device can include a framework composed of a biocompatible material; and a cover composed of the thin film nitinol that is attached to at least a portion of the framework.

The dielectric elastomer can be polydimethylsiloxane.

The sensor component can have an etched overall pattern. The etched overall pattern can be a meandering curved mesh pattern.

The flow diverting device can be selected from the group consisting of a coil and a stent. The flow diverting device can be composed of a polymer.

The system can include a transmitter device, a flexible antenna and an external data receiver device, to continually transfer data through the antenna to the receiver device.

The sensor component can have a stacked configuration that includes a carrying substrate; a polymer deposited on the carrying substrate; polyimide deposited on the polymer; a first metallic layer deposited on the polyimide, having an etched pattern; the dielectric elastomer deposited on the first metallic layer; a second metallic layer deposited on the dielectric elastomer, having an etched pattern; and an encapsulate elastomer deposited as a final layer.

In another aspect, the invention includes a method of measuring blood flow in a vascular system of a patient body. The method includes forming an integrated sensor and flow diverter, which includes fabricating a flow diverter, including forming a framework having a surface and composed of a biocompatible material; and connecting a thin film nitinol cover to at least a portion of the surface of the framework; fabricating a sensor component, including forming a first metallic layer; depositing a dielectric elastomer on the first metallic layer; and depositing a second metallic layer on the dielectric elastomer; connecting the sensor component to at least a portion of the flow diverter to form the integrated sensor and flow diverter; deploying the integrated sensor and flow diverter in the patient body to a target site; and transferring data in real time from the integrated sensor and flow diverter to an external data receiving device.

The method can further include etching the first metallic layer and the second metallic layer to form an overall pattern.

The deploying of the integrated sensor and flow diverter can be achieved by employing a microdelivery catheter.

The target site can be in an aneurysm or in a blood vessel adjacent the aneurysm.

BRIEF DESCRIPTION OF THE DRAWINGS

A full understanding of the disclosed concept can be gained from the following description of the preferred embodiments when read in conjunction with the accompanying drawings, in which.

DETAILED DESCRIPTION OF PREFERRED EMBODIMENTS

Figure 1:
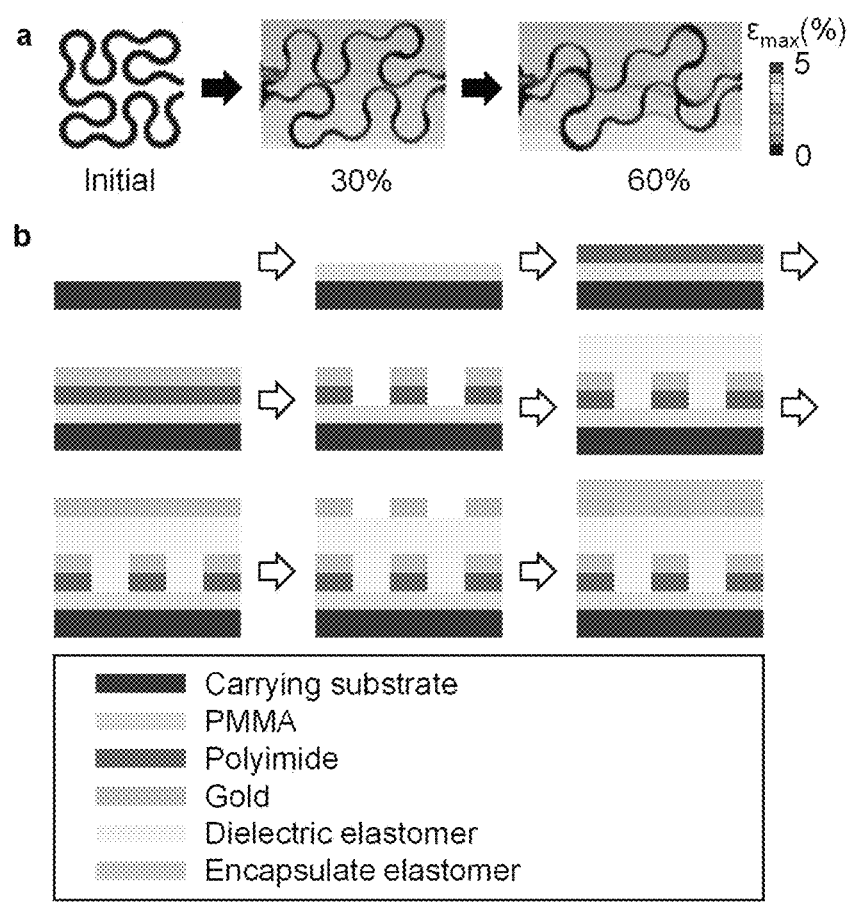
FIG. 1 is a schematic that shows fabrication of a capacitive microflow sensor, in accordance with certain embodiments of the invention.

The invention relates to devices, systems and methods to monitor hemodynamic alterations in the vascular system. The invention has an implantable sensor component, e.g., package, which includes micro flow sensor(s) to measure blood flow in the vascular system of a patient. The invention is particularly useful to monitor intra-/post-operative hemodynamic properties in the location of a cerebral aneurysm and, hemodynamic alterations following placement of a device for treating ischemic diseases in carotid, coronary and peripheral arteries.

The stretchable, microflow sensor component of the invention is combined or conformally integrated with a flow diverting device. Suitable sensor components for use in the invention include ultra-low profile, non-thrombogenic, wireless, microflow capacitive sensors that are constructed of a highly stretchable material. Furthermore, the sensor component can include a pattern etched by techniques, such as but not limited to, photolithography. Suitable flow diverting devices are known in the art to reduce blood flow in a vascular system, e.g., vessel or aneurysm sac, and include coils and stents. In accordance with the invention, the sensor component is combined or conformally integrated with, e.g., connected, attached or mounted to a portion of, the flow diverting device to form a "smart" flow diverter, which is utilized to monitor cerebral aneurysm hemodynamics in blood vessels.

The invention can be employed in procedures and treatments for cerebral aneurysm and ischemic diseases in carotid, coronary and peripheral arteries. The procedures and treatments include placing the flow diverter device in the vascular system of a patient. In accordance with the invention, during the procedure for placement of the flow diverter device, the sensor component is integrated with the flow diverter device. The sensor component is effective to measure flow velocity reduction and gauge the progressive effectiveness of packing during placement. Post-procedurally, the sensor component being integrated the flow diverter device in the vascular system of the patient, is effective to continuously monitor in real time intra-/post-operative hemodynamic properties around the cerebral aneurysm and hemodynamic alterations. The "smart" flow diverter can quantitatively measure the incoming flow rate to the sac to evaluate the efficacy and progress of the aneurysm treatment process.

With respect to treating the aneurysm, presence of the sensor component inside the patient body is effective to monitor non-invasively the aneurysm until intra-aneurysmal hemodynamic quiescence is achieved. The sensor component may be placed into the aneurysm to monitor blood flow within the sac. Alternately, the sensor component may be placed in a blood vessel adjacent to the aneurysm to measure blood flow or velocity in the blood vessel. Continual monitoring of blood flow in the aneurysm or in an adjacent vessel can provide information on re-narrowing of the treated area.

The sensor component can include a capacitive microflow sensor or sensor array. The sensor can be patterned, e.g., have a pattern etched by a technique, such as but not limited to, photolithography. The sensor(s) is wireless, non-thrombogenic, and ultra-low profile to achieve continuous monitoring of intra-/post-operative hemodynamic alterations in real time. For example, an array of sensors can be integrated with, e.g., mounted on the surface of, a coil or stent. Changes in blood flow either in the aneurysm sac or in the adjacent blood vessel result in capacitance changes in the array of wireless, non-thrombogenic, highly stretchable, ultra-low profile, microflow capacitive sensors, such that blood flow is continuously monitored.

The flow diverting device, e.g., coil or stent, is composed of a biocompatible material. There are a variety of materials known in the art that are suitable for constructing the flow diverting device. In certain embodiments, the flow diverting device includes a bendable, stretchable material, such as but not limited to, thin film nitinol (TFN). The stretchability and bendability of a microfabricated TFN allows for safe deployment to a neurovascular target site, e.g., an aneurysm. Non-limiting examples include thin film nitinol (TFN) flow diverters, such as, TFN stents. The flow diverter device can include a framework. In certain embodiments, the flow diverter device includes a framework composed of metal, metal alloy or polymer, and a cover or layer composed of superhydrophilic nitinol, such as, in the form of TFN.

In certain embodiments, a stretchable, microflow capacitive sensor component is integrated with a TFN, e.g., TFN covered, flow diverter to form the "smart" flow diverter, in accordance with certain embodiments of the invention.

The invention also includes transmitting and receiving devices for continuous transfer of data that is obtained from the sensors. A transmitter is integrated with the sensor component/flow diverter to transfer data from the sensor(s) through a flexible antenna to an external data receiver device. For example, wireless telemetry components, e.g., using LC resonator circuits, can continuously transfer data on hemodynamic alterations to an external data acquisition system.

According to the invention, the sensor component includes a metallic material and a flexible dielectric material. The metallic material can be a thin metallic layer. The sensor component can include a top metallic layer and a bottom metallic layer. The flexible dielectric material or layer can be positioned between the top and bottom metallic layers. The flexible dielectric material is deposited or applied to the surface of the thin metallic layer. The thin metallic layer is composed of, e.g., formed from, metal or metal alloys that are known in the art. Suitable examples include, but are not limited to, gold, magnesium, nickel-titanium (nitinol) and blends thereof. A metallic layer can be in the form of a thin film or a nanomembrane. The metallic, e.g., metal or metal alloy, layers can have an overall pattern etched by a conventional technique known in the art, such as, photolithography, for the flexible and stretchable capacitor. The dielectric material is a biocompatible, highly stretchable material, such as, but not limited to, a dielectric elastomer. A wide variety of elastomers, e.g., polyurethanes, are known in the art, which are suitable for use in this invention. In certain embodiments, the dielectric elastomer is polydimethylsiloxane (PDMS) and is deposited on, or applied to, the patterned metallic layer.

Capacitance changes are produced when the stretchable sensor is deflected locally due to the flow of blood. For example, a parallel plate capacitor can be employed, such that incoming blood flow deforms the dielectric layer, which results in the capacitance change. Furthermore, a LC oscillator transmitter can be employed to continuously transfer the change in capacitance, i.e., data, through a flexible coil antenna to an external data receiver. The sensor component being integrated with the flow diverter allows for blood to flow through the flow diverter, the sensor to be deflected as a result of the blood flow, the dielectric layer to be deformed, and a capacitance change to be generated and measured.

As mentioned, the sensor component includes the metallic, e.g., metal or metal alloy, layer that may have an etched overall pattern, and a layer of dielectric elastomer deposited thereon. In certain embodiments, the sensor component is a stacked configuration, e.g., parallel plate capacitor, that includes a carrying substrate as a base or lower layer, a first metallic layer deposited on the carrying substrate, the dielectric elastomer deposited on the first metallic layer, and a second metallic layer deposited on the dielectric elastomer. It is contemplated and understood that additional layers or materials may intervene between the carrying substrate, metallic layers and the dielectric elastomer, or to encapsulate the stacked configuration.

The integration of the stretchable microflow sensor and flow diverter, e.g., "smart" flow diverter, can be achieved using various designs, provided that the sensor is deflected and the dielectric deformed as a result of the flow of blood through the smart flow diverter, such that a change in capacitance is measurable. The stretchable microflow capacitive sensor can be connected or attached, e.g., mounted, to a portion of a surface of the flow diverter, e.g., an interior surface or an exterior surface, such as TFN, through which the blood flows.

In certain embodiments, the sensor component includes the following three stacked layers: metal/metal alloy layer, dielectric layer and metal/metal alloy layer for capacitive sensing of incoming flow in the blood vessel. The capacitive sensor can be assembled as a parallel plate capacitor. The sensor component of the invention can differ from standard solid plate capacitors as a result of the etched overall pattern used for this flexible and stretchable capacitor. The overall pattern of the sensor is not limiting and may include a meandering curved mesh pattern as shown in FIG. 1, view (a).

The sensor component can be fabricated using conventional microfabrication techniques. In general, the sensor can include a stacked configuration including metallic layers and a dielectric layer, and have an overall patterned form. A microfabrication method is shown in FIG. 1 view (b), in accordance with certain embodiments of the invention. In FIG. 1 view (b) the method of fabricating the microflow capacitive sensor component includes obtaining a carrying substrate. The carrying substrate can be chemically cleaned and treated, such as, with oxygen plasma. A layer of poly (methyl methacrylate) (PMMA) is applied to a top surface of the carrying substrate. This sacrificial polymer layer is not limited to PMMA. Suitable polymers for use in the fabrication process may be selected from a variety of polymers that are known in the art. In FIG. 1 view (b), deposited on the top surface of the PMMA layer, is a polyimide layer. These layers are deposited to form a stacked configuration. The capacitor is added to this base configuration. A bottom layer of the capacitor is sputtered onto the top surface of the base configuration, e.g., polyimide layer, and an overall pattern is etched. As shown in FIG. 1 view (b), the bottom layer of the capacitor is gold. The gold can be in the form of a gold nanomembrane. As mentioned, the bottom layer of the capacitor includes a metal or metal alloy selected from those known in the art. Non-limiting examples include gold, as well as, magnesium and nitinol, and blends thereof. The overall pattern may be etched in the bottom and polyimide layers by using photolithography techniques. The dielectric elastomer (e.g., polyurethane) layer is then deposited. A suitable dielectric elastomer is polydimethylsiloxane (PDMS). Subsequently, a top capacitor layer is applied to the surface of the dielectric elastomer layer, and the desired overall pattern is etched by using photolithography to overlap the bottom layer. Thus, the dielectric elastomer is "sandwiched" between two metallic layers. An encapsulate elastomer layer then may be deposited thereon. Various known elastomers can be used. A suitable encapsulate elastomer includes, but is not limited to, silicone elastomer.

Figure 2:
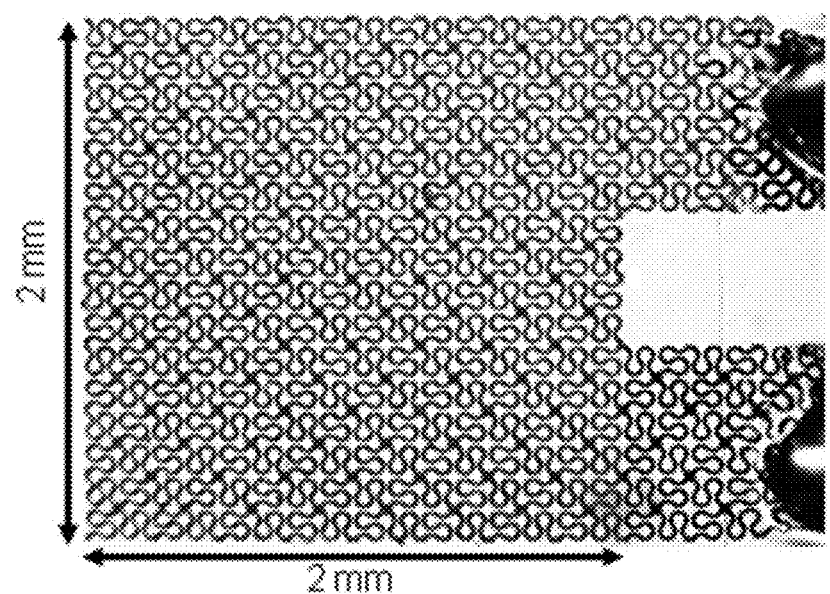
FIG. 2 shows an optical top view image of a fabricated capacitive microflow sensor, in accordance with certain embodiments of the invention.

FIG. 2 is an optical image showing a top view of a fabricated capacitive microflow sensor having an overall pattern, in accordance with certain embodiments of the invention.

Figure 3:
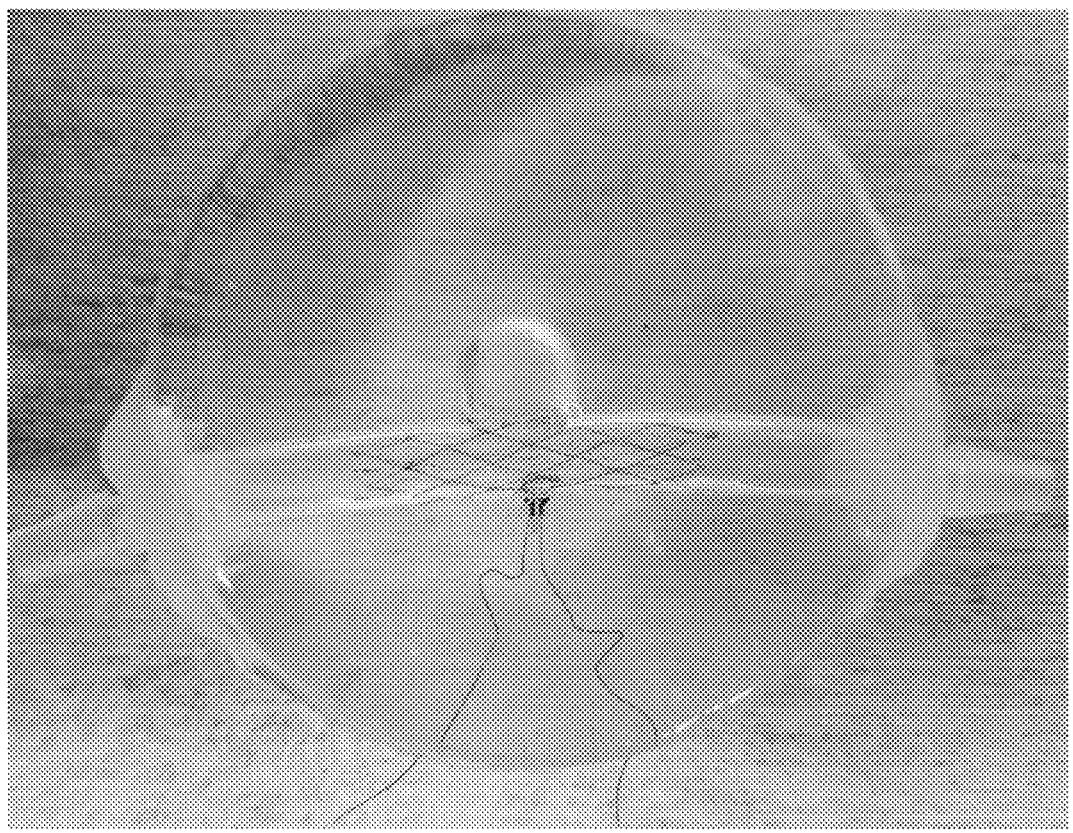
FIG. 3 shows a sensor positioned within an aneurysm model, in accordance with certain embodiments of the invention.

FIG. 3 is an image showing a smart flow diverter in an aneurysm model. The aneurysm sac is shown, and the flow diverter with the sensor partially attached thereto is positioned at the entrance of the aneurysm sac.

The combined sensor component and flow diverter device, e.g., "smart" flow diverter, can be deployed in the patient body at the target site. For an aneurysm, the smart flow diverter is deployed either within the aneurysm, or within an adjacent blood vessel. The sensor portion of the "smart" flow diverter is utilized to monitor cerebral aneurysm hemodynamics in the blood vessel. The sensor component has extremely flexible and stretchable mechanical properties for safe utilization in treating neurovascular aneurysms. For example, cerebral endovascular procedures typically require a 1.7 Fr microdelivery catheter, i.e., having an outer diameter of only 0.56 mm. Thus, the flexibility of the sensor of the invention allows for it to be positionable within the catheter for deployment at the target site. The deployed, integrated microflow capacitive sensor can quantitatively measure the incoming flow rate to the aneurysm sac, to evaluate the efficacy and progress of the aneurysm treatment process.

Since it is understood and anticipated that the invention is particularly useful for monitoring cerebral aneurysms, which occur within the subarachnoid spaces of the brain that is surrounded by thick tissue and skull, e.g., 10-15 centimeters below the skin, the required mechanical and sensing properties of the sensor is both challenging and relevant to the invention.

Bulk nitinol, due to its ability to be encased into small catheters and subsequently deployed within the body, has been used in currently available medical devices. For example, bulk nitinol is currently used in stents, ASD closure devices, and vena cava filters. However, the delivery systems for bulk nitinol are relatively large (compared to thin film) due to the physical dimensions of the device itself and the covering fabric, and require further refinement for use in emergencies. Thus, thin film nitinol (i.e., only a few micron thick), which is an order of magnitude smaller than bulk nitinol or gore-tex fabric, represents a suitable material for ultra-low profile vascular repair devices.

The integrated "smart" flow diverter can be combined with a delivery catheter system. The diverter can be cooled to a temperature below 5° C., to allow the nitinol material to be easily deformed (i.e., converting malleable martensite phase in nitinol). Once the diverter is deformed into a collapsed geometry, the diverter is inserted into the delivery catheter, which is typically a hollow cylindrical tube having a relatively small inner diameter. The type of delivery catheter is not critical to the use of the invention. Standard, off-the-shelf delivery systems may be employed to deploy the diverter in vitro. When the diverter is deployed and exposed to the blood temperature, the diverter conformally deploys in the pulmonary artery area with its superelastic property (i.e., self-expanding), and subsequently is retrievable.

The TFN for use in the invention can be fabricated using conventional processes and apparatus known in the art. In certain embodiments, suitable TFN for use in the invention is fabricated by a DC sputter deposition technique using a near equiatomic nitinol target under ultra-high vacuum atmosphere. "Hot-target" sputter deposition and micropatterning to create thin film nitinol with fenestrations can be conducted as follows. Photoresist is deposited on a (4-inch) silicon wafer in a desired or pre-selected micropattern. A deep reactive ion etching technique is used to create trenches (50 micrometers in depth) around the photoresist. The etching rate varies and can be approximately one minute for each one micrometer in depth. After removing the photoresist layer, a sacrificial layer of copper followed by an inhibitory silicon dioxide layer are deposited. Then, the thin film nitinol is sputter deposited on sheets (e.g., 6 micrometer in thickness) and removed from the silicon oxide layer. Following deposition and removal, the film is crystallized (e.g., for 120 minutes at 500° C.) in a vacuum (e.g., of less than $1\times10^{-7}$ Torr). The thin film nitinol material used in the invention can have an austenite finish temperature of about 34° C. The film can undergo a final cleaning treatment consisting of sequential rinsing in acetone, methanol, and ethanol (for five minutes) prior to use.

Following the microfabrication of TFN, the surface of the TFN structure can be treated using a hydrogen peroxide to make the surface superhydrophilic, which provides hemocompatibility. Microstructured TFN can accommodate stretchability in the radial direction and bendability upon 180 degrees with negligible effect to the structure. These properties allow for the fabrication of a stretchable microflow sensor in accordance with the invention.

The materials and membranes used for fabrication of the devices according to the invention can be combined with or without the use other materials, such as glue, suturing materials, other metallic wires, and welding (or soldering) materials. For example, adhesive materials, such as, glue, or suturing materials, such as, thread, may be used to connect the membrane to the superelastic structure. In terms of geometry of the devices, they should be sufficiently low profile, as well as deployable and retrievable in the vascular regions. Attaching thin film nitinol on a metallic backbone frame can be achieved by either stitching or suturing methods. Integration options including microscale mechanical clamping, microscale suturing, and direct deposition of the micro-patterned TFN membrane onto a framework. In certain embodiments, the TFN is connected to a nitinol stent framework by (1) suturing using ultra-thin nitinol or polymer thread (i.e., <100 µm thick) and/or (2) encapsulation of thin film nitinol sections directly onto the nitinol stent frame.

EXAMPLES

I. TFN Flow Diverter

Figure 4:
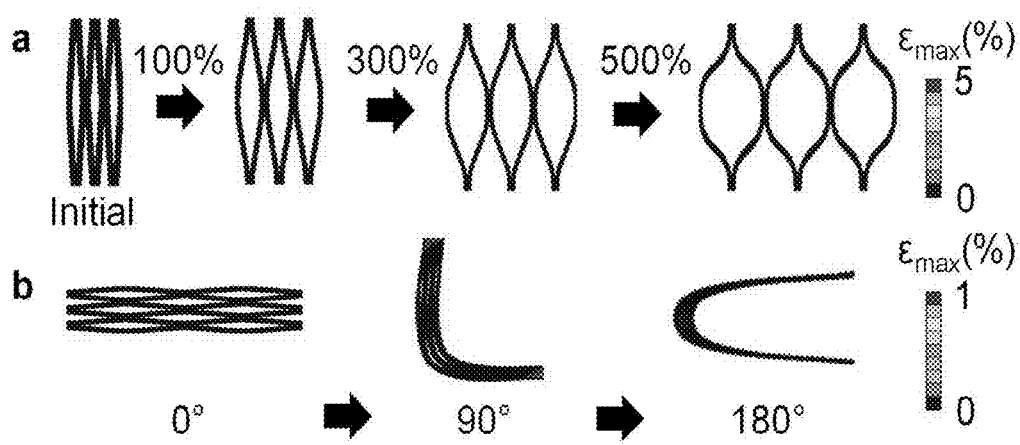
FIG. 4 includes images that show finite element modeling results of microstructured TFN upon applied tensile strains and bending, in accordance with the invention.
Figure 5:
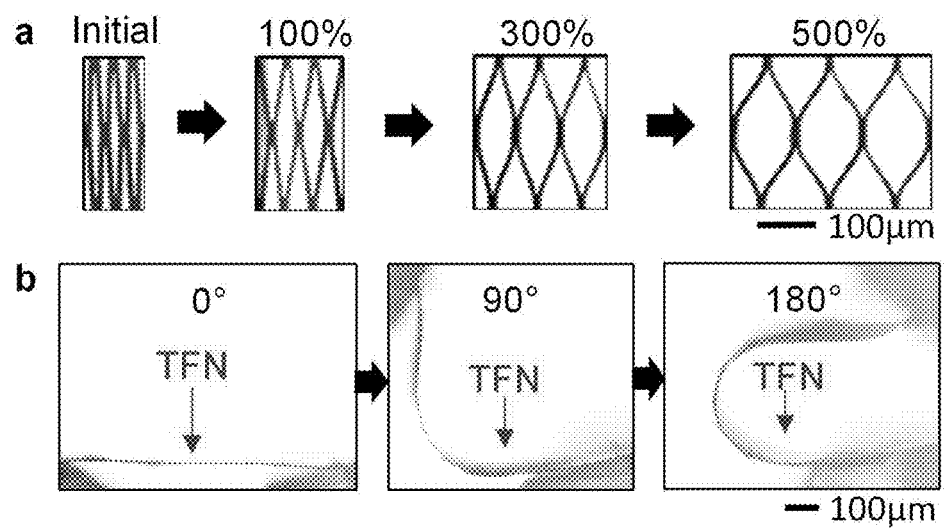
FIG. 5 shows optical images of mechanical testing of TFN, in accordance with certain embodiments of the invention.

A hyper-elastic TFN was fabricated using sputter deposition and conventional microfabrication. After the microfabrication, the surface of the TFN structure was treated by using a hydrogen peroxide to make the surface superhydrophilic, which provided hemocompatibility for in vitro and in vivo testing. Through the finite element analysis (FEA), there was determined the hyper-elasticity of the TFN stent and the equivalent mechanical testing. FIG. 4 shows the FEA results of the TFN modeling in tensile strains and bending. The microstructured TFN was found to accommodate stretchability up to 500% in the radial direction (see FIG. 4, view (a)) and an extreme bendability upon 180° with negligible effect to the structure (see FIG. 4, view (b)). To validate the structural safety of the TFN, estimated by the FEA study, a series of experimental validations were conducted. The mechanical testing of the TFN was assessed using a home-made mechanical stretcher, which consisted of the sample being connected to one fixed and one adjustable block. For the radial stretching, the TFN sample was aligned so that strain was applied only along its width (circumferentially/radially). Then, the adjustable side was incrementally moved to increase distance between the two slides, therefore increasing strain on the sample. Strain was monitored using visual and electrical recordings to ensure that structural integrity was maintained. Highly sensitive electrical recording was used illustrate the structural integrity of the sample where any fracturing or deformation would cause electrical fluctuations. The bending test used a similar procedure as the radial stretching, instead the sample was incrementally bent from 0° to 180° (with a soft "U" shape bend at 180°). FIG. 5, views (a) and (b), includes a set of images of the mechanical testing with the TFN sample. These tests caused no noticeable strain on the sample, visually or electrically, which confirmed the mechanical stability predicted by the FEA.

II. Microflow Sensor

A stretchable microflow sensor was fabricated by integrating two approaches of nanomaterial transfer printing and materials integration on a soft elastomer. This microflow sensor included three layers, consisting of 300 nm Au-2 µm dielectric layer-300 nm Au for capacitive sensing of incoming flow in the blood vessel. The capacitive sensor was assembled as a parallel plate capacitor. Apart from standard solid plate capacitors, a meandering curved mesh pattern was used for flexible and stretchable capacitor. The computational study based on the FEA was conducted to estimate the mechanical safety of the sensor structure upon the integration with the coil or TFN, which showed good stretchability, more than 50%.

FIG. 1, view (b) shows the overall fabrication steps to make the capacitive microflow sensor. Firstly, a carrying substrate was chemically cleaned and treated with oxygen plasma, then a sacrificial polymer layer (poly(methyl methacrylate)) was deposited as well as the polyimide. The bottom layer of the capacitor was then sputtered onto the substrate and the overall pattern (unit cell section of FIG. 1, view (a) "Initial" meandering pattern) was etched by using photolithography techniques. The polyimide layer was then etched using oxygen plasma to match the meandering pattern. The dielectric layer was deposited followed by a top capacitor layer, and the same process was used to etch the desired pattern to overlap the bottom layer. At this point for experimental testing, two micro-cables were attached to each capacitor layer, and then the final encapsulating layer was deposited.

A top view of the completed capacitive microflow sensor is shown in FIG. 2, with the dimensions of the capacitive area and attachment points of micro-flexible cables. The capacitive area is 2×2 mm with a 49% coverage due to the open meshed pattern, giving an equivalent area (A) of 1.96 mm². The elastomer used had a dielectric value ($\varepsilon_r$) of 2.5, giving an expected calculated capacitance of 21.69 pF.

Equation (1) is used to derive the expected capacitance (C) where (d) is the distance of the dielectric layer (approximately 2 µm in this case), and $\varepsilon_0$ is the dielectric constant.

$$C = \varepsilon_0 \varepsilon_r \frac{A}{d} \quad (1)$$

Figure 6:
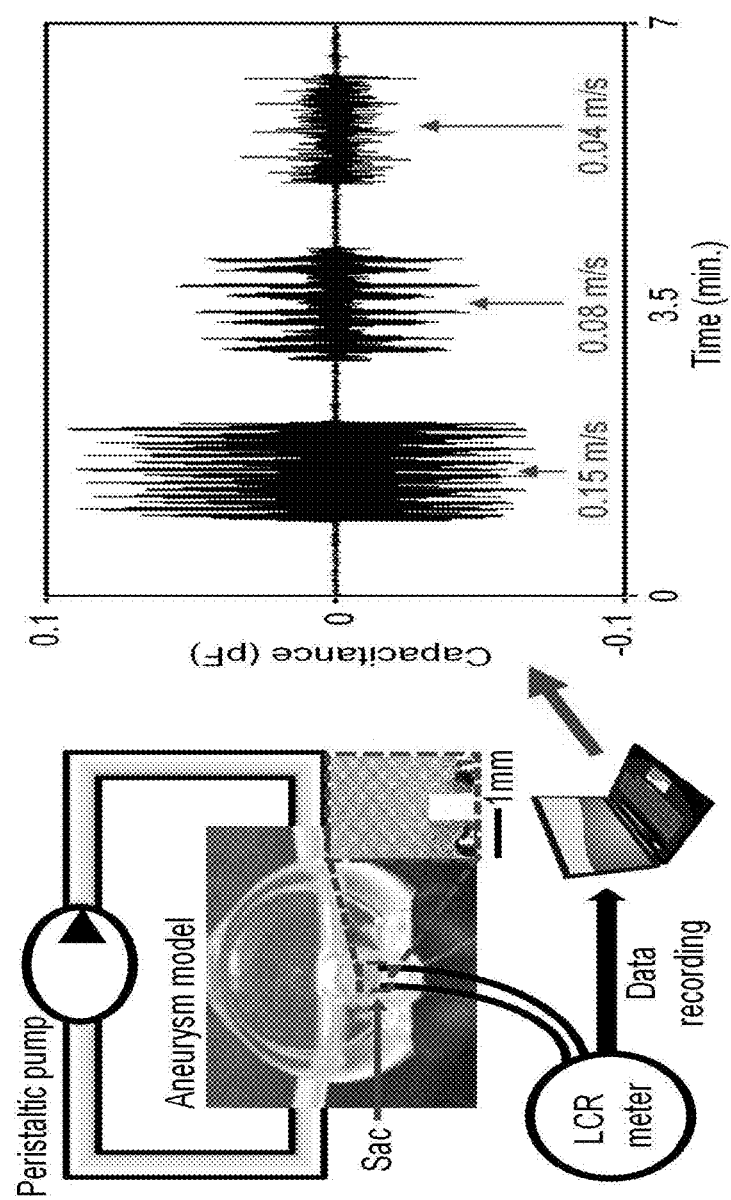
FIG. 6 shows in-vitro experiment setup to measure incoming flow to a sac using a capacitive microflow sensor, in accordance with the invention.

The measured capacitance of the fabricated flow sensor was 20.76 pF, which differs slightly from the calculated value due to the approximation of the dielectric layer. For in vitro testing of the flow sensor, the micro-flexible cables were connected to an LCR meter to measure the capacitance change upon variation of flow rates. An aneurysm model was created using a silicon polymer and tubing. The tubing used had an inner diameter of 3.175 mm allowing for the calculation of flow rate as velocity (m/s). FIG. 6 shows the in vitro experimental setup including the aneurysm model with embedded flow sensor inside the sac, peristaltic pump (FH100, Thermo Scientific), a highly precise LCR meter (4285A, Agilent), and data acquisition interface (LabVIEW, National Instruments). The peristaltic pump generated various flow rates to test the sensitivity of the sensor and the LCR meter measured the change of capacitance at 75 kHz using voltage of 100 mV in response to the selected flow rate. The data acquisition interface indicates a correlation between flow rate and measured capacitance allowing for monitoring of blood flow, where three select flow rates (40, 20, and 10 rpm; 10 rpm is measured to be equivalent to 0.302 mL/s) are shown. In the experimental setup, velocity can be calculated using the velocity formula for volumetric flow (q) in a pipe with inner diameter (d) which is 3.175 mm.

$$v = \frac{4q}{\pi d^2} \quad (2)$$

Equation (2) allows calculation of the velocity (v) of the fluid moving through the closed system at the specified volumetric flow rates (1.208, 0.604, and 0.302 mL/s). The resulting velocities for the specified flow rates are calculated to be 0.15, 0.08, and 0.04 m/s, respectively.

The average blood flow velocity range of the main carotid artery is between 0.1 and 0.5 m/s. Depending on the location, the mean velocity flow at the neck region of the aneurysm is around 0.25 to 0.3 m/s. With a target sensitivity of 0.1 m/s or lower, the microflow sensor will be able to distinguish and monitor the blood flow rate into the aneurysm sac over time. FIG. 5 shows the normalized graph of the tested flow rates over 7 minutes time, indicating clear differences in the capacitance fluctuation in response to different flow rates.

III. Conclusions

The elastic behavior of a microstructured TFN flow diverter was demonstrated through computational modeling and experimental mechanical testing. The results show ideal flexibility and stretchability of the TFN for the use in the treatment of neurovascular aneurysms. A capacitive microflow sensor has been fabricated and tested in vitro to show good sensitivity (maximum detection limit: 0.04 m/s). This sensing capability allows for monitoring the flow rate in an aneurysmal sac over the course of its occlusion. This study presents the feasibility of the smart flow diverter that offers an active, ultrasensitive monitoring of hemodynamics over time. For active monitoring of the intra-hemodynamics, the TFN flow diverter will include the microflow sensor that can be partially mounted on the surface of the device. Integration of the microflow sensor will allow for non-invasive, lower cost, long-term monitoring for the course of an aneurysm treatment process. In addition, future work includes device optimization through analytical and computational study and integration with wireless powering and data transmission in a stretchable platform.

Whereas particular embodiments of the invention have been described herein for purposes of illustration, it will be evident to those skilled in the art that numerous variations of the details may be made without departing from the invention as set forth in the appended claims.

What is claimed is:

1. An endovascular medical implant system positioned in a vascular system of a patient, comprising:
   a flow diverting device, comprising a thin film nitinol; and
   a wireless, non-thrombogenic, highly stretchable, ultra-low profile, microflow capacitive sensor component, comprising:
   a first metallic layer comprising an etched overall pattern, connected to at least a portion of the flow diverting device;
   a dielectric elastomer layer deposited on the first metallic layer; and
   a second metallic layer comprising an etched overall pattern, deposited on the dielectric elastomer layer,
   wherein the first metallic layer, the dielectric elastomer layer and the second metallic layer are in a stacked configuration, and
   wherein the capacitive sensor component is structured to produce a capacitive change when the capacitive sensor component is deflected by a flow of blood and the dielectric elastomer layer is deformed, and structured to measure a flow rate of the blood.

2. The system of claim 1, wherein each of the first and second metallic layers is selected from the group consisting of gold, magnesium, nitinol and blends thereof.

3. The system of claim 1, wherein the flow diverting device comprises:
   a framework composed of a biocompatible material; and
   a cover composed of the thin film nitinol that is attached to at least a portion of the framework.

4. The system of claim 1, wherein the dielectric elastomer is polydimethylsiloxane.

5. The system of claim 1, wherein the flow diverting device is selected from the group consisting of a coil and a stent.

6. The system of claim 1, wherein the flow diverting device is composed of a polymer.

7. The system of claim4 1 wherein the etched overall pattern is a meandering curved mesh pattern.

8. The system of claim 1, further comprising a transmitter device, a flexible antenna and an external data receiver device, to continually transfer data through the antenna to the receiver device.

9. The system of claim 1, wherein the sensor component has a stacked configuration, comprising:
   a carrying substrate;
   a polymer deposited on the carrying substrate;
   polyimide deposited on the polymer;
   the first metallic layer deposited on the polyimide, having an etched pattern;
   the dielectric elastomer deposited on the first metallic layer;
   the second metallic layer deposited on the dielectric elastomer, having an etched pattern; and
   an encapsulate elastomer deposited as a final layer.

10. A method of measuring blood flow in a vascular system of a patient body, comprising:
    forming an integrated sensor and flow diverter, comprising:
    fabricating a flow diverter, comprising:
    forming a framework having a surface and composed of a biocompatible material; and
    connecting a thin film nitinol cover to at least a portion of the surface of the framework;
    fabricating a microflow sensor component, comprising:
    forming a first metallic layer comprising an etched overall pattern;
    connecting the first metallic layer to at least a portion of the flow diverting device;
    depositing a dielectric elastomer on the first metallic layer; and
    depositing a second metallic layer on the dielectric elastomer comprising an etched overall pattern;
    connecting the microflow sensor component to at least a portion of the flow diverter to form the integrated sensor and flow diverter,
    wherein the first metallic layer, the dielectric elastomer and the second metallic layer are in a stacked configuration;
    deploying the integrated sensor and flow diverter in the patient body to a target site;
    deflecting the microflow sensor component with a flow of blood and deforming the dielectric elastomer layer, resulting in the microflow sensor component producing a capacitive change and measuring a flow rate of the blood; and
    transferring data in real time from the integrated sensor and flow diverter to an external data receiving device.

11. The method of claim 10, further comprising etching the first metallic layer and the second metallic layer to form an overall pattern.

12. The method of claim 10, wherein the deploying of the integrated sensor and flow diverter is achieved by employing a microdelivery catheter.

13. The method of claim 10, wherein the target site is in an aneurysm or in a blood vessel adjacent the aneurysm.

* * * * *